(12) United States Patent
Gao et al.

(10) Patent No.: US 12,121,476 B2
(45) Date of Patent: Oct. 22, 2024

(54) CORNEAL LENTICULAR INCISION USING A FEMTOSECOND LASER WITH SMOOTH SCANNING TRAJECTORY CONNECTING MULTIPLE SWEEPS

(71) Applicant: AMO Development, LLC, Irvine, CA (US)

(72) Inventors: Wenzhi Gao, Union City, CA (US); Hong Fu, Pleasanton, CA (US)

(73) Assignee: AMO Development, LLC, Irvine, CA (US)

( * ) Notice: Subject to any disclaimer, the term of this patent is extended or adjusted under 35 U.S.C. 154(b) by 374 days.

(21) Appl. No.: 17/658,229

(22) Filed: Apr. 6, 2022

(65) Prior Publication Data

US 2023/0320898 A1    Oct. 12, 2023

(51) Int. Cl.
*A61F 9/008*       (2006.01)

(52) U.S. Cl.
CPC .......... *A61F 9/008* (2013.01); *A61F 9/00827* (2013.01); *A61F 2009/0087* (2013.01); *A61F 2009/00872* (2013.01); *A61F 2009/00897* (2013.01)

(58) Field of Classification Search
CPC .................. A61F 9/008; A61F 9/00827; A61F 2009/0087; A61F 2009/00872; A61F 2009/00897
See application file for complete search history.

(56) References Cited

U.S. PATENT DOCUMENTS

| | | | |
|---|---|---|---|
| 7,921,852 B2 | 4/2011 | Gerlach et al. | |
| 9,017,315 B2 | 4/2015 | Rathjen | |
| 9,456,925 B2 | 10/2016 | Kurtz et al. | |
| 10,213,339 B2 | 2/2019 | Muehlhoff et al. | |
| 10,369,052 B2 | 8/2019 | Fu | |
| 10,548,768 B2 | 2/2020 | Pallikaris | |
| 10,842,674 B2 | 11/2020 | Fu et al. | |
| 11,071,648 B2 | 7/2021 | Muehlhoff et al. | |
| 2007/0282313 A1 | 12/2007 | Huang et al. | |
| 2011/0206072 A1 | 8/2011 | Karavitis | |
| 2016/0089270 A1 | 3/2016 | Fu | |
| 2019/0159933 A1 | 5/2019 | Romano et al. | |
| 2020/0046558 A1 | 2/2020 | Fu et al. | |

(Continued)

FOREIGN PATENT DOCUMENTS

| CN | 102292055 A | 12/2011 |
|---|---|---|
| WO | 2020039328 A1 | 2/2020 |

*Primary Examiner* — Jonathan T Kuo

(74) *Attorney, Agent, or Firm* — Johnson & Johnson Surgical Vision, Inc.

(57) ABSTRACT

An ophthalmic laser system and related method for forming a lenticular incision in a corneal lenticule extraction procedure. The lenticular incision is formed by multiple sweeps of a laser scan line along meridians of longitude of the lenticular incision, where the end point of each sweep is connected to the start point of the next sweep by a smooth turning trajectory. The trajectory includes a first circular arc tangentially connected to the first sweep at its end point, a second circular arc tangentially connected to the next sweep at its start point, and a straight line segment tangentially connected to both circular arcs. The smooth trajectory is determined with the given limits of velocity, acceleration and jerk of the XY scanning motors, without using high frequency filters to smooth the trajectory, thereby avoiding unknown changes to the original trajectory and achieving high precision lenticule shapes.

14 Claims, 10 Drawing Sheets

(56) References Cited

U.S. PATENT DOCUMENTS

| | | |
|---|---|---|
| 2020/0188166 A1 | 6/2020 | Buck et al. |
| 2020/0337903 A1 | 10/2020 | Fu et al. |
| 2021/0015668 A1 | 1/2021 | Malek Tabrizi et al. |
| 2021/0052420 A1 | 2/2021 | Rathjen |
| 2021/0121323 A1 | 4/2021 | Stobrawa et al. |
| 2021/0128358 A1 | 5/2021 | Fu et al. |
| 2022/0096274 A1 | 3/2022 | Fu et al. |

CORNEAL LENTICULAR INCISION USING A FEMTOSECOND LASER WITH SMOOTH SCANNING TRAJECTORY CONNECTING MULTIPLE SWEEPS

BACKGROUND OF THE INVENTION

Field of the Invention

Embodiments of this invention relate generally to laser-assisted ophthalmic procedures, and more particularly, to systems and methods for lenticular incisions in the cornea.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (hereinafter "LASIK"), photorefractive keratectomy (hereinafter "PRK") and corneal lenticule extraction.

In the LASIK procedure, an ultra-short pulsed laser is used to cut a corneal flap to expose the corneal stroma for photoablation with ultraviolet beams from an excimer laser. Photoablation of the corneal stroma reshapes the cornea and corrects the refractive condition such as myopia, hyperopia, astigmatism, and the like. In a PRK procedure where no flap is created, the epithelium layer is first removed, and some stroma material is then removed by an excimer laser. The epithelium layer will grow back within a few days after the procedure.

In a corneal lenticule extraction procedure, instead of ablating corneal tissue with an excimer laser following the creation of a corneal flap, the technique involves tissue removal with two or more femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision. Methods for corneal lenticule extraction using a fast-scan-slow-sweep scheme of a surgical ophthalmic laser system are described in U.S. Pat. Appl. Pub. No. 20160089270, entitled "Systems And Methods For Lenticular Laser Incision," published Mar. 31, 2016, and U.S. Pat. Appl. Pub. No. 20200046558, entitled "High Speed Corneal Lenticular Incision Using A Femtosecond Laser," published Feb. 13, 2020.

SUMMARY

Embodiments of the present invention provide a lenticular incision method using a scanning method in which sweeps along meridians of longitude are connected to each other by smooth trajectories to significantly reduce acceleration and jerk in the movement of the XY scanner.

In one aspect, embodiments of the present invention provides an ophthalmic surgical laser system which includes: a laser source configured to generate a pulsed laser beam comprising a plurality of laser pulses; a laser delivery system configured to deliver the pulsed laser beam to a target tissue in a subject's eye; a high frequency scanner configured to scan the pulsed laser beam back and forth at a predefined frequency; an XY-scanner configured to deflect the pulsed laser beam, the XY-scanner being separate from the high frequency scanner; a Z-scanner configured to modify a depth of a focus of the pulsed laser beam; and a controller configured to control the laser source, the high frequency scanner, the XY-scanner and the Z-scanner to successively form a plurality of sweeps which collectively form at least one lenticular incision of a lens in the subject's eye, the lens having a curved surface that defines an apex and a central axis passing through the apex, wherein each sweep is formed by: controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the central axis and has a defined distance to the apex, and controlling the XY-scanner and the Z-scanner to move a center of the scan line along a meridian of longitude of the lens, the meridian of longitude being a curve that passes through the apex and has a defined angular position around the central axis; and wherein the plurality of sweeps are successively formed one after another along the respective meridians of longitude which are different from one another; and wherein the controller is further configured to control the XY-scanner to move the center of the scan line along a smooth turning trajectory that connects an end point of a first one of the plurality of sweeps to a start point of a second one of the plurality of sweeps, the turning trajectory including a first circular arc, a straight line segment, and a second circular arc, wherein the first circular arc is tangentially connected to the first sweep at the end point of the first sweep, the second circular arc is tangentially connected to the second sweep at the start point of the second sweep, and the straight line segment is tangentially connected to both the first and second circular arcs.

In preferred embodiments, the controller is further configured to control the laser source and/or the laser delivery system to blank the pulsed laser beam when the center of the scan line is moved along the turning trajectory from the end point of the first sweep to the start point of the second sweep.

In another aspect, embodiments of the present invention provide a method for creating a lenticular incision using an ophthalmic surgical laser system, the method including the steps of: generating, by a laser source, a pulsed laser beam comprising a plurality of laser pulses; delivering the pulsed laser beam to a target tissue in a subject's eye; scanning, by a high frequency scanner, the pulsed laser beam back and forth at a predefined frequency; deflecting, by an XY-scanner, the pulsed laser beam, the XY-scanner being separate from the high frequency scanner; modifying, by a Z-scanner, a depth of a focus of the pulsed laser beam; and controlling, by a controller, the laser source, the high frequency scanner, the XY-scanner and the Z-scanner to successively form a plurality of sweeps which collectively form at least one lenticular incision of a lens in the subject's eye, the lens having a curved surface that defines an apex and a central axis passing through the apex, including forming each sweep by: controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the central axis and has a defined distance to the apex, and controlling the XY-scanner and the Z-scanner to move a center of the scan line along a meridian of longitude of the lens, the meridian of longitude being a curve that passes through the apex and has a defined angular position around the central axis, and controlling the laser source to periodically blank the pulsed laser beam when the scan line is located within a central area of the lens, wherein the plurality of sweeps are successively formed one after another along the respective meridians of longitude which are different from one another; and controlling, by the controller, the XY-scanner to move the center of the scan line along a smooth turning trajectory that connects an end point of a first one of the plurality of sweeps to a start point of a second one of the plurality of sweeps, the turning trajectory including a first circular arc, a straight line segment, and a second circular arc, wherein the first circular arc is tangentially connected to the first sweep at the end point of the first sweep, the second circular arc is tangentially connected to the second sweep at the start point of the second sweep, and the straight line segment is tangentially connected to both the first and second circular arcs.

In preferred embodiments, the controller controls the laser source and/or the laser delivery system to blank the pulsed laser beam when the center of the scan line is moved along the turning trajectory from the end point of the first sweep to the start point of the second sweep.

It is to be understood that both the foregoing general description and the following detailed description are exemplary and explanatory and are intended to provide further explanation of the invention as claimed.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

DETAILED DESCRIPTION OF PREFERRED EMBODIMENTS

Embodiments of this invention are generally directed to systems and methods for laser-assisted ophthalmic procedures, and more particularly, to systems and methods for corneal lenticule incision.

Figure 1:
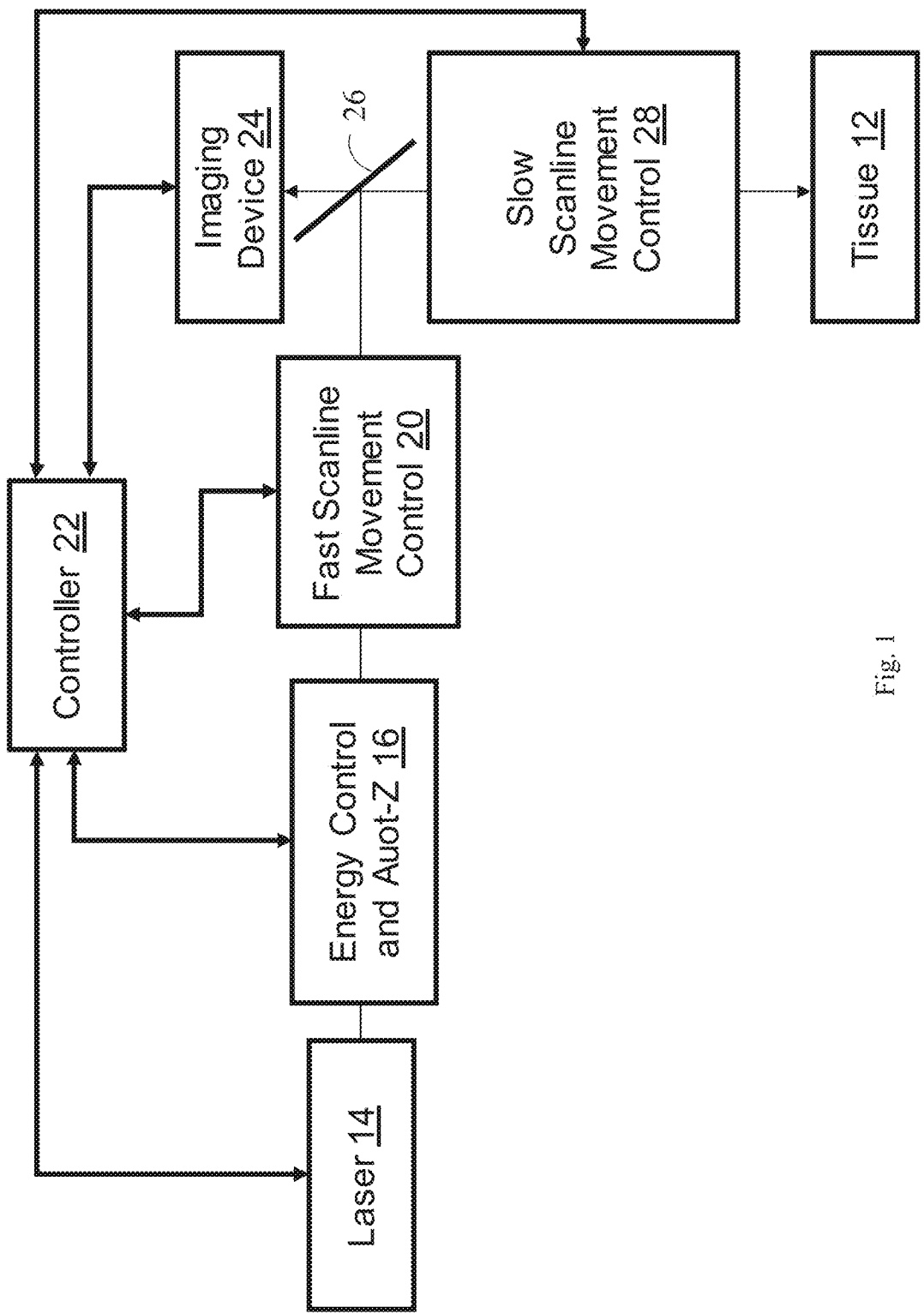
FIG. 1 is a block diagram of a surgical ophthalmic laser system which may be used to perform a lenticule incision method according to an embodiment of the present invention.

Referring to the drawings, FIG. 1 shows a system 10 for making an incision in a tissue 12 of a patient's eye. The system 10 includes, but is not limited to, a laser 14 capable of generating a pulsed laser beam, an energy control module 16 for varying the pulse energy of the pulsed laser beam, a fast scanline movement control module 20 for generating a fast scanline of the pulsed laser beam (described in more detail later), a controller 22, and a slow scanline movement control module 28 for moving the laser scanline and delivering it to the tissue 12. The controller 22, such as a processor operating suitable control software, is operatively coupled with the fast scanline movement control module 20, the slow scanline movement control module 28, and the energy control module 16 to direct the scanline of the pulsed laser beam along a scan pattern on or in the tissue 12. In this embodiment, the system 10 further includes a beam splitter 26 and a imaging device 24 coupled to the controller 22 for a feedback control mechanism (not shown) of the pulsed laser beam. Other feedback methods may also be used. In an embodiment, the pattern of pulses may be summarized in machine readable data of tangible storage media in the form of a treatment table. The treatment table may be adjusted according to feedback input into the controller 22 from an automated image analysis system in response to feedback data provided from a monitoring system feedback system (not shown).

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the tissue or other material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam toward the eye.

Figure 2:
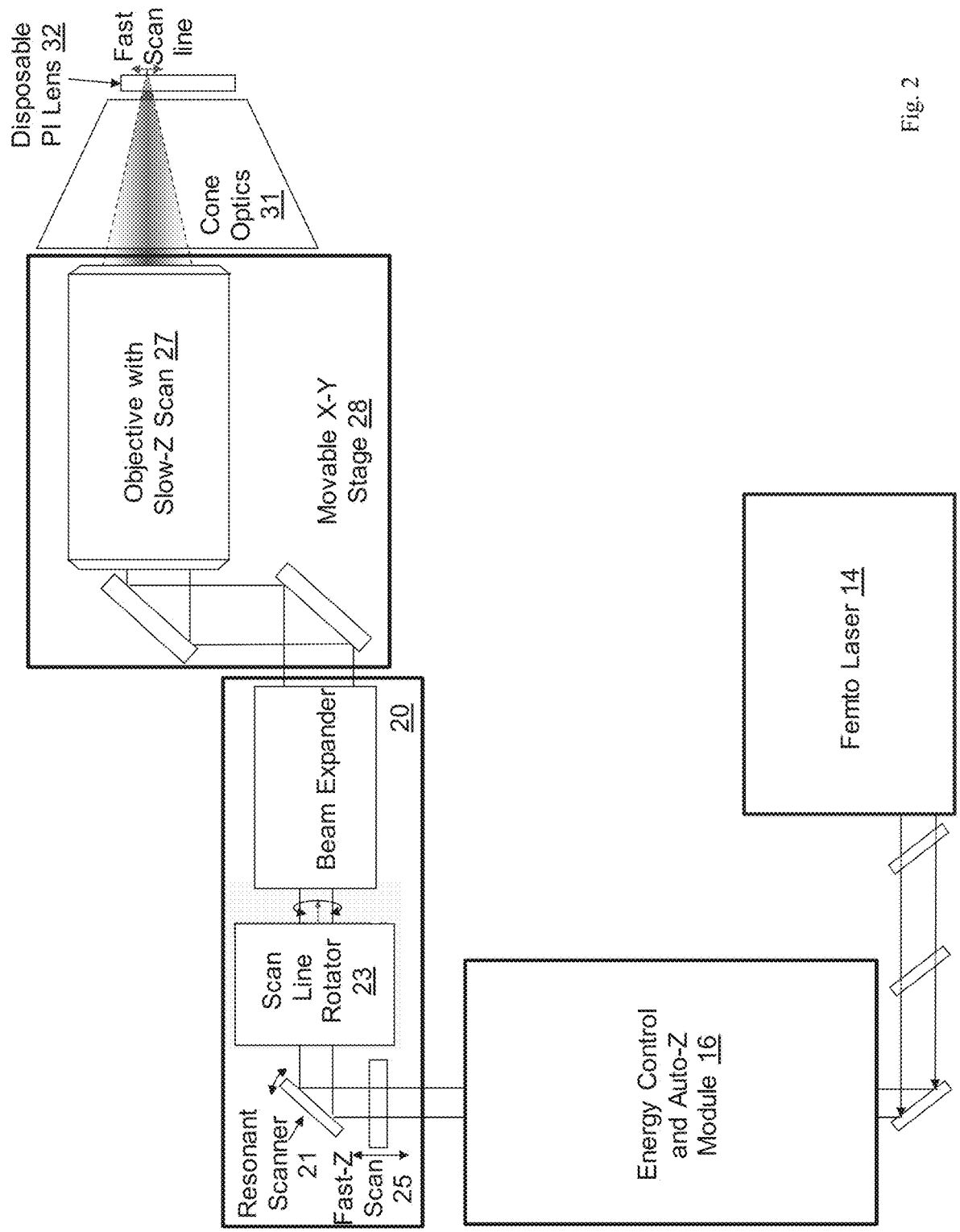
FIG. 2 is another diagram of a surgical ophthalmic laser system which may be used to perform a lenticule incision method according to an embodiment of the present invention.

FIG. 2 shows another exemplary diagram of the laser system 10. FIG. 2 shows components of a laser delivery system including a moveable XY-scanner (or movable XY-stage) 28 of a miniaturized femtosecond laser system. In this embodiment, the system 10 uses a femtosecond oscillator, or a fiber oscillator-based low energy laser. This allows the laser to be made much smaller. The laser-tissue interaction is in the low-density-plasma mode. An exemplary set of laser parameters for such lasers include pulse energy in the 40-100 nJ range and pulse repetitive rates (or "rep rates") in the 2-40 MHz range. A fast-Z scanner 25 and a resonant scanner 21 direct the laser beam to a scanline rotator 23. When used in an ophthalmic procedure, the system 10 also includes a patient interface design that has a fixed cone nose 31 and a contact lens 32 that engages with the patient's eye. A beam splitter may be placed inside the cone 31 of the patient interface to allow the whole eye to be imaged via visualization optics. In some embodiments, the system 10 may use: optics with a 0.6 numerical aperture (NA) which would produce 1.1 μm Full Width at Half Maximum (FWHM) focus spot size; and a resonant scanner 21 that produces 0.2-1.2 mm scan line with the XY-scanner scanning the resonant scan line to a 1.0 mm field. The prism 23 (e.g., a Dove or Pechan prism, or the like) rotates the resonant scan line in any direction on the XY plane. The fast-Z scanner 25 sets the incision depth. The slow scanline movement control module employs a movable XY-stage 28 carrying an objective lens with Z-scanning capability 27, referred to as slow-Z scanner because it is slower than the fast-Z scanner 25. The movable XY-stage 28 moves the objective lens to achieve scanning of the laser scanline in the X and Y directions. The objective lens changes the depth of the laser scanline in the tissue. The energy control and auto-Z module 16 may include appropriate components to control the laser pulse energy, including attenuators, etc. It may also include an auto-Z module which employs a confocal or non-confocal imaging system to provide a depth reference. The miniaturized femtosecond laser system 10 may be a desktop system so that the patient sits upright while being under treatment. This eliminates the need of certain opto-mechanical arm mechanism(s), and greatly reduces the complexity, size, and weight of the laser system. Alternatively, the miniaturized laser system may be designed as a conventional femtosecond laser system, where the patient is treated while lying down.

Figure 3:
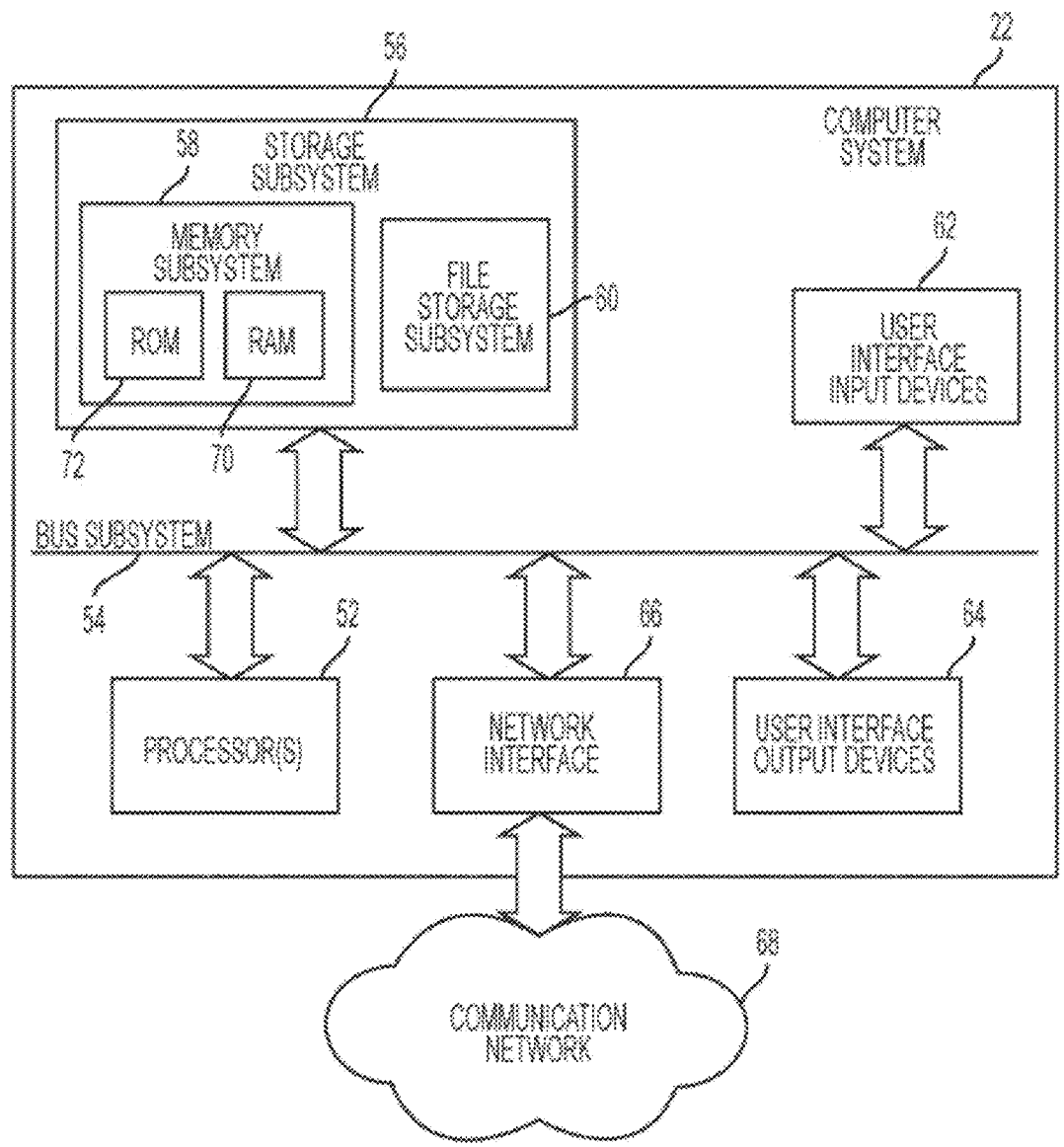
FIG. 3 is a simplified diagram of a controller of a surgical ophthalmic laser system which may be used to perform a lenticule incision method according to an embodiment of the present invention.

FIG. 3 illustrates a simplified block diagram of an exemplary controller 22 that may be used by the laser system 10 according to an embodiment of this invention to control the laser system 10 and execute at least some of the steps discussed in detail below. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 3 is intended only as an example for purposes of illustrating only one embodiment of the present invention. Many other configurations of controller 22, having more or fewer components than those depicted in FIG. 3, are possible.

As should be understood by those of skill in the art, additional components and subsystems may be included with laser system 10. For example, spatial and/or temporal integrators may be included to control the distribution of energy within the laser beam. Ablation effluent evacuators/filters, aspirators, and other ancillary components of the surgical laser system are known in the art, and may be included in the system. In addition, an imaging device or system may be used to guide the laser beam.

Figure 4:
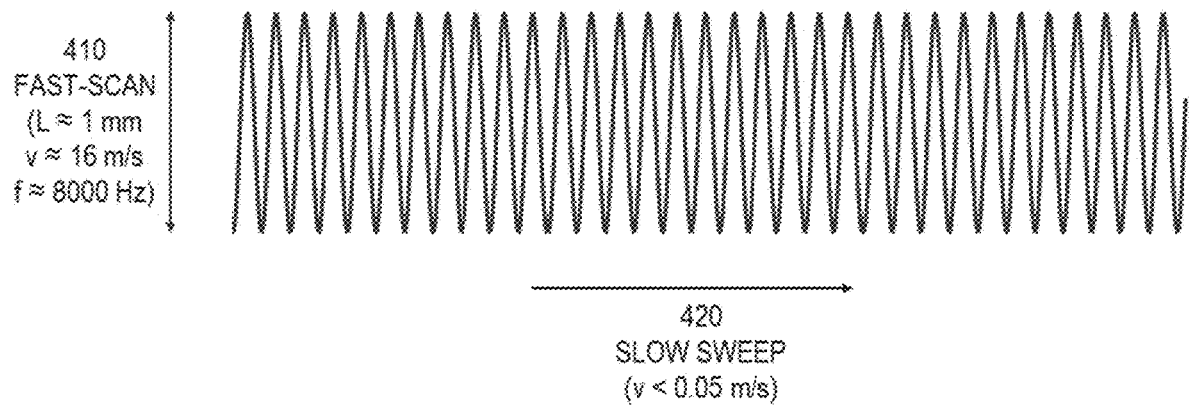
FIG. 4 illustrates an exemplary scanning of a surgical ophthalmic laser system according to an embodiment of the present invention.

In preferred embodiments, the beam scanning can be realized with a "fast-scan-slow-sweep" scanning scheme, also referred herein as a fast-scan line scheme. The scheme consists of two scanning mechanisms: first, a high frequency fast scanner is used to scan the beam back and forth to produce a short, fast scan line (e.g., a resonant scanner 21 of FIG. 2); second, the fast scan line is slowly swept by much slower X, Y, and Z scan mechanisms (e.g. the moveable X-Y stage 28 and the objective lens with slow-Z scan 27, and the fast-Z scanner 25). FIG. 4 illustrates a scanning example of a laser system 10 using an 8 kHz (e.g. between 7 kHz and 9 kHz, or more generally, between 0.5 kHz and 20 kHz) resonant scanner 21 to produce a fast scan line 410 of about 1 mm (e.g., between 0.9 mm and 1.1 mm, or more generally, between 0.2 mm and 1.2 mm) and a scan speed of about 25 m/sec, and X, Y, and Z scan mechanisms with the scan speed (sweeping speed) smaller than about 0.1 m/sec. The fast scan line 410 may be perpendicular to the optical beam propagation direction, i.e., it is always parallel to the XY plane. The trajectory of the slow sweep 420 can be any three dimensional curve drawn by the X, Y, and Z scanning devices (e.g., XY-scanner 28 and fast-Z scanner 25). An advantage of the "fast-scan-slow-sweep" scanning scheme is that it only uses small field optics (e.g., a field diameter of 1.5 mm) which can achieve high focus quality at relatively low cost. The large surgical field (e.g., a field diameter of 10 mm or greater) is achieved with the XY-scanner, which may be unlimited.

Figure 5:
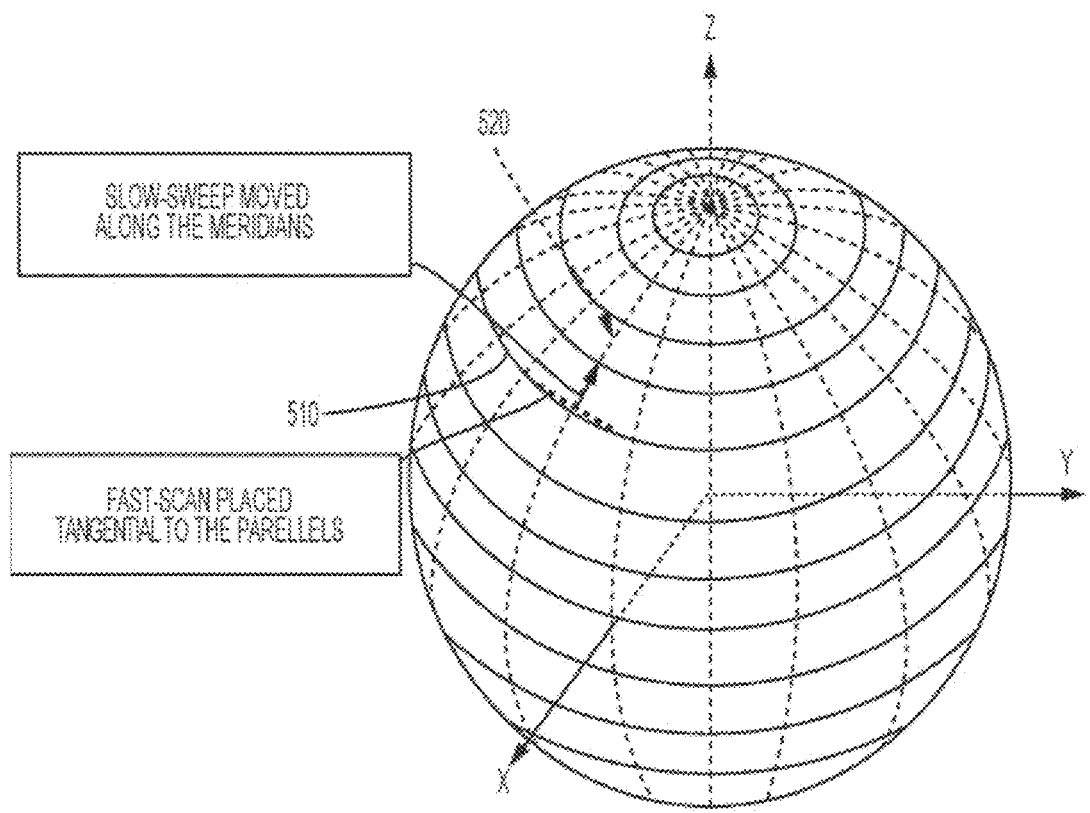
FIG. 5 illustrates an exemplary surface dissection using a fast-scan-slow-sweep scheme of a surgical ophthalmic laser system according to an embodiment of the present invention.
Figure 7:
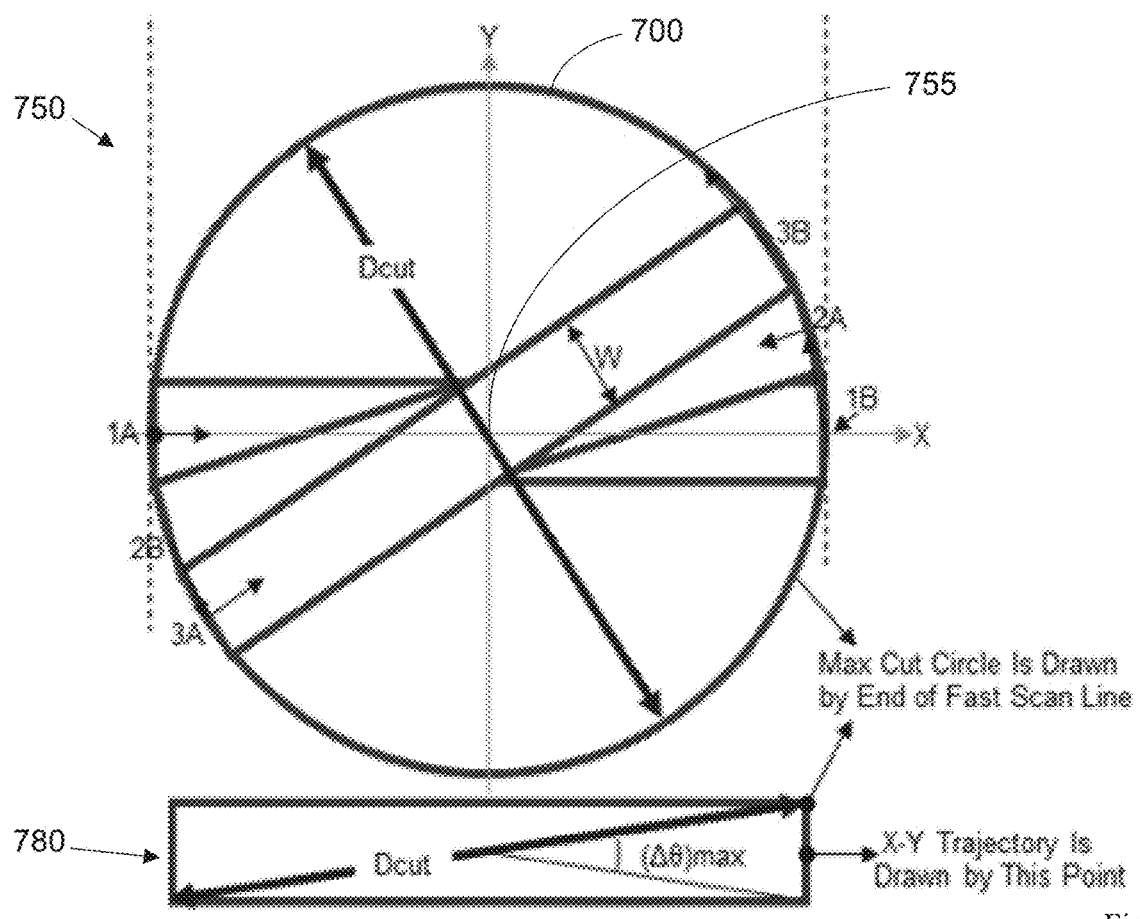
FIG. 7 illustrates an exemplary lenticular incision using a surgical ophthalmic laser system according to an embodiment of the present invention.

In a preferred embodiment shown in FIGS. 5 and 7, the laser system 10 creates a smooth lenticular cut using the "fast-scan-slow-sweep" scanning scheme under a preferred procedure. First, in a three dimensional lenticular cut, the fast scan line is preferably placed tangential to the parallels of latitude 510 on the surface of the lenticule. A parallel of latitude is the intersection of the surface with a plane perpendicular to the Z axis (which is the axis parallel to the depth direction of the eye), i.e. a circle on the surface of the lens that is perpendicular to the Z axis and has a defined distance to the apex (the highest point in the Z direction). For example, in the laser system 10 of FIG. 2, this can be realized by adjusting a prism 23 to the corresponding orientations via software, e.g., via the controller 22. Second, the slow sweep trajectory preferably moves along the meridians of longitude 520 on the surface of the lenticule. A meridian of longitude is the intersection of the surface with a plane that passes through the Z axis, i.e. a curve that passes through the apex and has a defined angular direction with respect to the Z axis. For example, in the laser system of FIG. 2, this can be done by coordinating the XY scanner 28, and the Fast-Z scanner 25 via the software, e.g., via the controller 22. The procedure starts with the scan line being parallel to the XY plane, and sweeps through the apex of the lens, following the curvature with the largest diameter (see also FIG. 7). Multiple sweeps are performed at successive angular directions with respect to the Z axis, for example as realized by rotating the prism 23 between successive sweeps, to form the entire lenticule. With this preferred procedure, there are no vertical "steps" in the dissection, and vertical side cuts are eliminated. As will be analyzed herein below, the deviations between the laser focus locations and the intended spherical surface dissections are also minimized.

Figure 6:
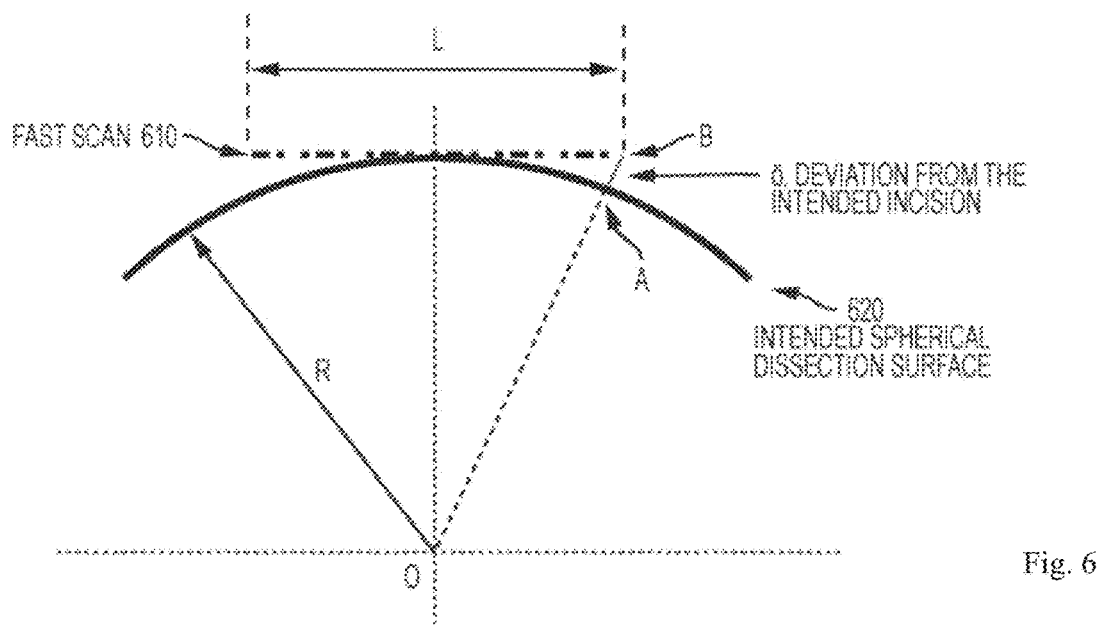
FIG. 6 illustrates a geometric relation between a fast-scan line and an intended spherical dissection surface of a surgical ophthalmic laser system according to an embodiment of the present invention.

FIG. 6 shows the geometric relation between the fast scan line 610 and the intended spherical dissection surface 620, e.g., of a lens, especially the distance deviation ($\delta$) between the end point B of the scan line 610 and point A on the intended dissection surface 620. The maximum deviation $\delta$ is the distance between point A and point B, and is given by (Equation (1)):

$$\delta = \sqrt{R^2 + \frac{L^2}{4}} - R \approx \frac{L^2}{8R}$$

where R is greater than L. R is the radius of curvature of the surface dissection 620, and L is the length of the fast scan.

While the above maximum deviation analysis is for a spherical surface, this scanning method may also be used to create a smooth cut having a non-spherical shape, such as an ellipsoidal shape, etc. In such a case, the parallel of latitude and/or the meridian of longitude may not be circular.

In an exemplary case of myopic correction, the radius of curvature of the surface dissection may be determined by the amount of correction, $\Delta D$, using the following equation (Equation (2)):

$$\Delta D = \frac{(n-1)}{R_1} + \frac{(n-1)}{R_2}$$

where n=1.376, which is the refractive index of cornea, and $R_1$ and $R_2$ (may also be referred herein as $R_t$ and $R_b$) are the radii of curvature for the top surface and bottom surface of a lenticular incision, respectively. For a lenticular incision with $R_1=R_2=R$ (the two dissection surfaces are equal for them to physically match and be in contact), we have (Equation (3)):

$$R = \frac{2(n-1)}{\Delta D}$$

Using such a "fast-scan-slow-sweep" scanning scheme, each sweep of the fast scan line forms a bent band, the bent band being the equivalent of bending a flat rectangle such that its long sides form arched shapes (the shape of the meridian of longitude) while its short sides remain straight. FIG. 7 is a top view 750 of a lenticular incision 700 and a top view 780 of one exemplary sweep. $D_{CUT}$ indicates the incision diameter and w indicates the width of the sweeps.

FIG. 7 illustrates three exemplary sweeps (1A to 1), (2A to 2B) and (3A to 3B), each going through (i.e., going over) the lenticular incision apex 755. To form these sweeps, the trajectory of the center point of the scan line moves along a meridian of the incision 700 from a start point 1A on the periphery to an opposite end point 1B on the periphery, then move from point 1B to a nearby start point 2A on the periphery (in a counter-clockwise direction), them move along a meridian of the incision to an opposite end point 2B on the periphery, then move from point 2B to a nearby start point 3A on the periphery (in a counter-clockwise direction), them move along a meridian of the incision to an opposite end point 3B on the periphery, etc.

According to embodiments of the present invention, when moving the center point of the scan line from the end point of one sweep (e.g. 1B) to the start point of the next sweep (e.g. 2A), rather than moving along a straight line connecting the two points, the center point is moved along a curve that is smooth and corner-free. As described earlier, the center of the scan line is moved by the movable XY-stage 28 and fast-Z scanner 25 of the ophthalmic laser system. Moving the center point from each end point to the next start point in a straight line would form many sharp turning points which would introduce undesirable high acceleration and jerk (the rate of change of acceleration) for the XY-stage motion. In the mechanical system of the XY-stage, large changes in velocity and acceleration require large changes in the XY actuator torques, which in turn can cause highly jerky motion and severe vibrations in the stage. This may result in high trajectory error and undesirable system vibration. In embodiments of the present invention, by moving from the end point to the next start point in a corner-free smooth trajectory, the irregularity and magnitude of the acceleration and jerk are greatly reduced, thus improving the corneal lenticular incision quality. This is done without unnecessarily slowing down the movement along the trajectory, so the overall time required of the lenticular incision is not significantly increased.

Figure 8:
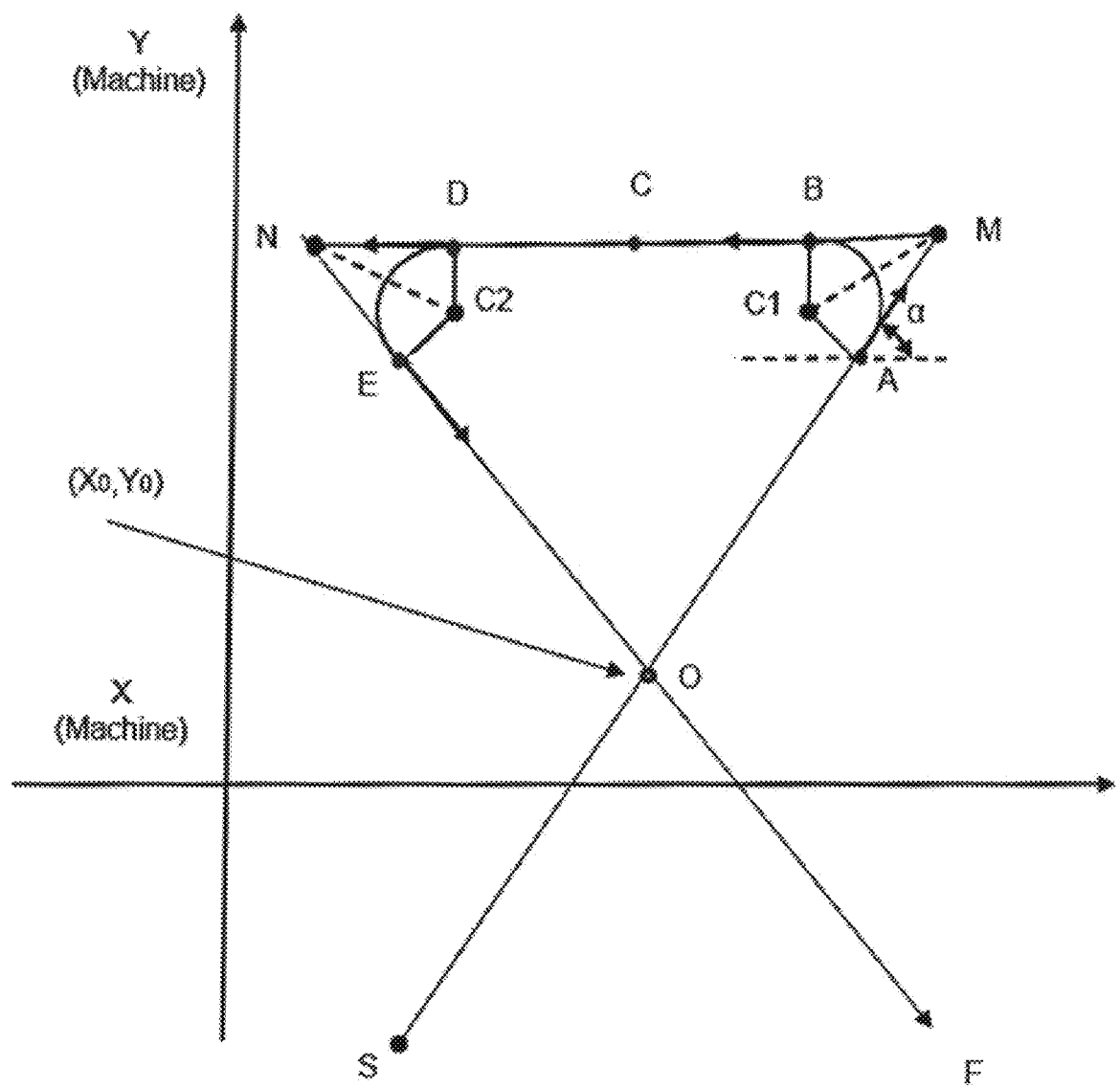
FIG. 8 is a schematic diagram that illustrates an exemplary corner-free smooth turning trajectory for connecting two sweeps according to an embodiment of the present invention.

FIG. 8 schematically illustrates an exemplary corner-free smooth turning trajectory (i.e. the movement of the center point of the scan line) according to embodiments of the present invention. In FIG. 8, a first sweep proceeds along a trajectory from point S via apex O to point A, and the next sweep proceeds along a trajectory from point E via apex O to point F. The end point A of the first sweep is smoothly connected to the start point E of the next sweep by a turning trajectory A-B-D-E, where AB is a circular arc, BD is a straight line, and DE is another circular arc. The first circular arc AB is tangential to both line OA and line BD; the second circular arc DE AB is tangential to both line BD and line EO. The entire curve including the two sweeps and the turning trajectory A-B-D-E is differentiable.

In FIG. 8, point M is the intersection of extensions of straight lines OA and DB, and point N the intersection of extensions of straight lines OE and DB. These points are used in the computation as described below, but it should be noted that line segments AM, MB, DN, and NE are not parts of the turning trajectory. The X and Y coordinate system shown in FIG. 8 is the machine coordinate system defined by the laser system.

The conditions and steps for computing the turning trajectory are described below.

The coordinates $(X_O, Y_O)$, $(X_M, Y_M)$ and $(X_N, Y_N)$ of point G, point M and point N, respectively, are given as input for the computation. In some embodiments, points M and N are at equal distances from the apex G, but this is not required. The constraints used in the computation include:

(1) Geometric configurations: The distance from point M to the straight line segment connecting points A and B (i.e. the chord of the circular arc AB) should be within a predefined limit, ZW. (2) Acceleration and velocity: The velocity and acceleration at the turning points A and B should be within predefined limits. The magnitude of the linear velocity of the movement at point A (the entry point of the circular arc AB) and the magnitude of the velocity at point B (the exit point of the circular arc AB) are preferably equal. Preferably, the magnitude of the linear velocity of the movement along the entire turning trajectory is approximately a constant.

As the circular arc AB is tangential to line OA at point A and tangential to line BD at point B, line C1A is perpendicular to line OM and line C1B is perpendicular to line DM, where C1 is the center of the circle that defines the circular arc AB. The coordinates $(X_{C1}, Y_{C1})$ of circular center C1 and the radius r of the circular arc AB are computed as follows.

The angle $\alpha$ of line segment OM in the (X, Y) coordinate system is:

$$\alpha = \arctan(\text{slope}_{OM})$$

where $$\text{slope}_{OM} = \frac{Y_M - Y_O}{X_M - X_O}.$$

Similarly, the angle of line segment NM in the (X, Y) coordinate system is:

$$\beta = \arctan(\text{slope}_{NM})$$

where $$\text{slope}_{NM} = \frac{Y_M - Y_N}{X_M - X_N}.$$

The angle ∠OMN, or $\gamma$, is:

$$\gamma = \arccos\left(\frac{OM^2 + NM^2 - ON^2}{2 * OM * NM}\right)$$

where $$OM = \sqrt{(X_O - X_M)^2 + (Y_O - Y_M)^2}$$

$$NM = \sqrt{(X_N - X_M)^2 + (Y_N - Y_M)^2}$$

$$ON = \sqrt{(X_O - X_N)^2 + (Y_O - Y_N)^2}$$

As an example, using the maximum value ZW as the distance from point M to the chord AB, the length of line segment AM is:

$$AM = \frac{ZW}{\cos\left(\frac{\gamma}{2}\right)}$$

The coordinates $X_A$ and $Y_A$ of point A is computed from the length of line segment AM and angle $\alpha$:

$$X_A = X_M - AM * \cos(\alpha)$$

$$Y_A = Y_M - AM * \sin(\alpha)$$

Similarly, the coordinates $X_B$ and $Y_B$ of point B is computed from the length of line segment BM (which is equal to the length of line segment AM) and angle β:

$$X_B = X_M - BM*\cos(\beta)$$

$$Y_B = Y_M - BM*\sin(\beta)$$

Based on the coordinates of $(X_A, Y_A)$ and $(X_B, Y_B)$, the length of chord AB is:

$$AB = \sqrt{(X_A - X_B)^2 (Y_A - Y_B)^2}$$

Then the radius r of the circle is computed as:

$$r = \frac{AB/2}{\cos\left(\frac{\gamma}{2}\right)}$$

The coordinates of the center C1 of the circle is:

$$X_{C1} = X_A - r*\sin(\alpha)$$

$$Y_{C1} = Y_A + r*\cos(\alpha)$$

From the computed center coordinates and radius value, the coordinates of the trajectory waypoints along the circular arc AB can be computed as:

$$X_i = X_{C1} - r*\sin(\alpha + i*\text{delta}\_\alpha)$$

$$Y_i = Y_{C1} + r*\cos(\alpha + i*\text{delta}\_\alpha)$$

where delta_α is an incremental angle value along the circular arc and i denotes the i-th sampling point after point A.

The incremental angle value delta_α may be computed from the values of the movement velocity (when a constant linear velocity is used) and a sampling frequency. Using the linear velocity $v_A$ at point A, which is assumed to be within the preset limits of velocity and acceleration, and the radius r of the circular arc, the angular velocity of the movement is:

$$\omega = v_A/r$$

Using the sample frequency, $f_s$, the incremental angle value is:

$$\text{delta}\_\alpha = \omega/f_s$$

The circular arc DE and coordinates of trajectory waypoints along it may be computed in a similar way. Then, the straight line segment is defined by point B (exit point of first circular arc AB) and point D (entry point of second circular arc DE), and the coordinates of the trajectory waypoints along line BD may be computed using the linear velocity and the sampling frequency.

Preferably, after computing the trajectory, Gaussian smoothing is applied to the trajectory data points by performing a convolution with a Gaussian kernel function. This smoothing step helps to suppress high frequency signals and enhance low frequency data. The Gaussian kernel function is defined by the equation below, in which a is the standard deviation of the sampled data points.

$$G(x) = \frac{1}{\sqrt{2\pi}\,\sigma} e^{-\frac{x^2}{2\sigma^2}}$$

The Gaussian kernel function has the following desirable properties: symmetric; smooth function with infinite number of derivatives; convolution of the Gaussian kernel function with itself is a Gaussian function; and 2D convolution can be performed by two 1D convolution.

Figure 9:
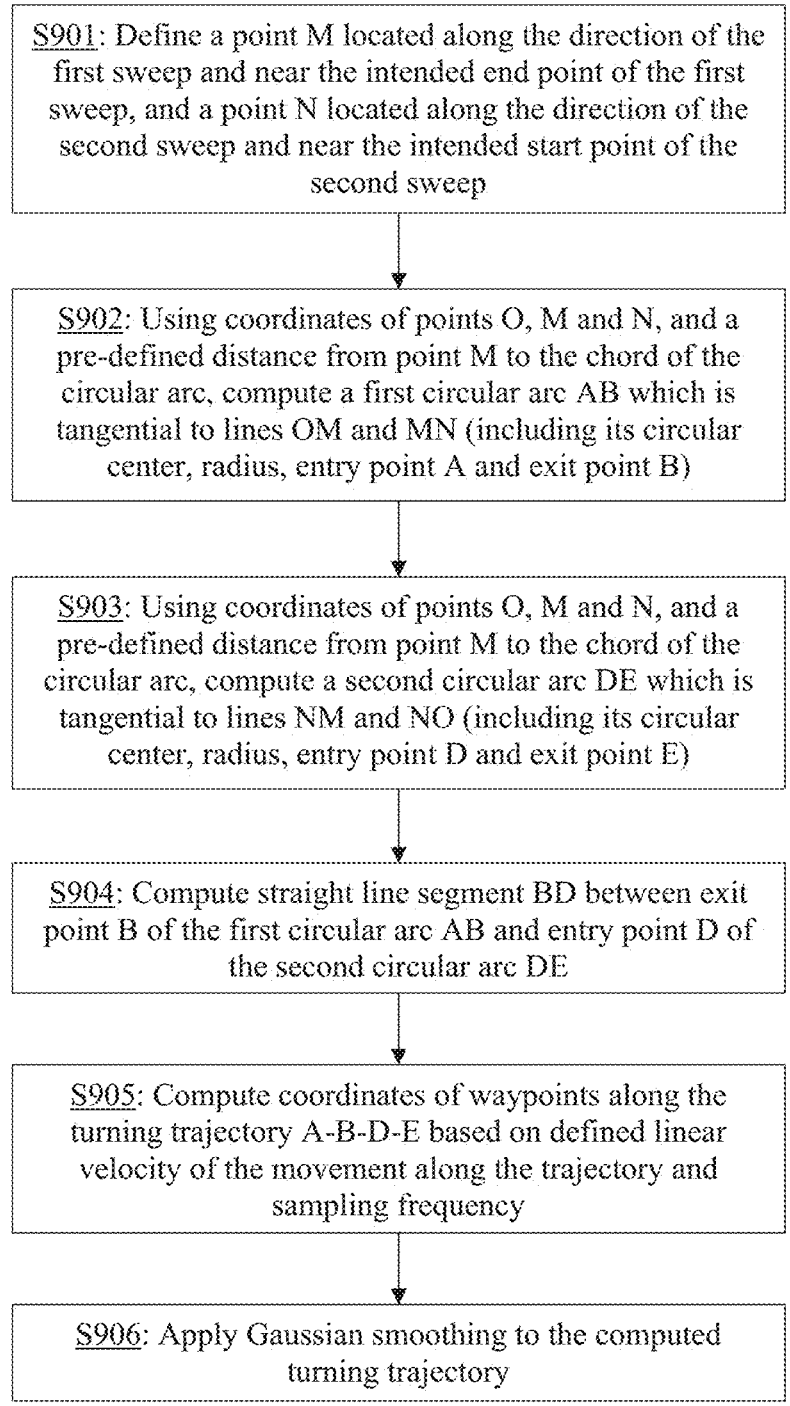
FIG. 9 is a flowchart illustrating a method of generating a smooth trajectory for connecting two sweeps according to an embodiment of the present invention.

The above-described computation of the smooth turning trajectory between two sweeps is summarized below with reference to the flowchart in FIG. 9. First, a point M located along the direction of the first sweep and near the intended end point of the first sweep, and a point N located along the direction of the second sweep and near the intended start point of the second sweep, are defined as input (step S901). Each of these points can be defined by an angular position of the respective sweep around the apex O and a distance from the apex, which is set to be slightly larger than a desired radius of the lenticular incision to be formed. The two reference points may be the same or different distances from the apex.

Then, using the coordinates of points O, M and N, and a pre-defined distance from point M to the chord of the circular arc, the circular center C1, radius r, entry point A and exit point B of a first circular arc AB (associated with point M) are computed, such that the circular arc AB is tangential to the line OM at entry point A and tangential to the line MN at exit point B (step S902). A second circular arc DE associated with point N is similarly computed, such that the circular arc DE is tangential to the line NM at entry point D and tangential to the line NO at exit point E (step S903). A straight line segment BD is formed between the exit point B of the first circular arc and the entry point D of the second circular arc (step S904). The first circular arc AB, the straight line segment BD, and the second circular arc DE together form a smooth, corner-free turning trajectory A-B-D-E connecting the end of the first sweep (point A) and the start of the next sweep (point E).

The coordinates of waypoints along the turning trajectory A-B-D-E may be computed based on a defined (preferably constant) linear velocity of the movement along the trajectory and a sampling frequency (step S905). Optionally, Gaussian smoothing is applied to the computed turning trajectory by performing a convolution with a Gaussian kernel function (step S906).

In the above-described embodiment, the coordinates of points M and N (the intersections of the directions of the two sweeps with the straight line segment of the smooth turning trajectory) are taken as input, and the coordinates of points A, B, D and E (the entry and exit points of the two circular arcs of the smooth turning trajectory) are computed, using the distance from points M, N to the chords of the corresponding circular arcs as a limiting geometric parameter. In a first alternative embodiment, the coordinates of points A and E (the entry point of the first circular arc and exit point of the second circular arc) are taken as input, and the coordinates of B and D (the exit point of the first circular arc and the entry point of the second circular arc) are computed, using the radius of the circles of the circular arcs as a limiting geometric parameter. More specifically, for the circular arc AB, the center C1 of the circle may be computed from the coordinates of the reference point A, the angle of line OA, and the radius r of the circle, based on the tangential relationship of the circle and line OA. The center C2 for the circular arc DE may be similarly computed. The coordinates of points B and D may then be computed from the direction of line C1C2 and the radius r, based on the tangential relationship between the straight line segment BD and the two circles.

In the above-described smooth turning trajectories, the circles of the two circular arcs have identical radii. In alternative embodiments, they may have different radii, so long as the tangential relationships between the circular arcs and the trajectories of sweeps as well as the straight line segment are maintained.

While it is possible to smoothly connect the two sweeps with differentiable curves in endless ways, embodiments of the present invention use a smooth turning trajectory that has two circular arcs connected by one straight line segment, with each circular arc being tangential to both the corresponding sweep trajectory and the straight line segment. Such a turning trajectory can be explicitly calculated from the pre-determined system's maximum speed, maximum acceleration, and jerk. In other words, the trajectory determined with this algorithm will automatically meet the systems motors characteristics. Comparing with normal general filtering technique for corner smoothing, the proposed method does not introduce implicit usually unknown changes to the originally intended trajectory. Therefore, with this algorithm, the shape precision of lenticule and system's maximum speed, acceleration, and maximum jerk can be achieved at the same time.

Figure 10:
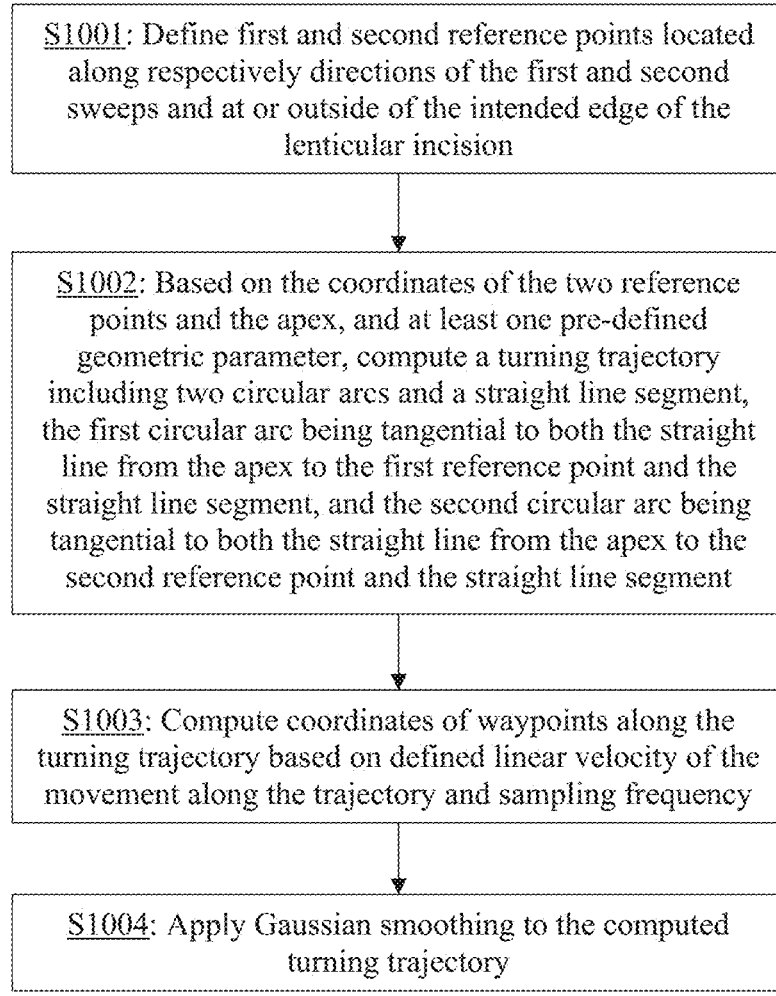
FIG. 10 is another flowchart illustrating a method of generating a smooth trajectory for connecting two sweeps according to embodiments of the present invention.

The flowchart in FIG. 10 is a more general summary of the methods of computing the smooth turning trajectory between two sweeps according to embodiments of the present invention. First, a first reference point located along the direction of the first sweep and at or outside of the intended edge of the lenticular incision, and a second reference point located along the direction of the second sweep and at or outside of the intended edge of the lenticular incision, are defined (step S1001). These reference points may be points M and N as in the embodiment of FIG. 9, or points A and E as in the first alternative embodiment, as described above. Each reference point may be defined by an angular position of the respective sweep around the apex of the lenticular incision and a distance from the apex.

Then, based on the coordinates of the two reference points as well as the coordinates of the apex, and at least one pre-defined geometric parameter, two circular arcs and a straight line segment are computed, such that the first circular arc is tangential to both the straight line from the apex to the first reference point and the straight line segment, and the second circular arc is tangential to both the straight line from the apex to the second reference point and the straight line segment (step S1002). The pre-defined geometric parameter may be a distance from the reference point to the chord of the corresponding circular arc as in the embodiment of FIG. 9, or the radius of the circle of the circular arc as in the first alternative embodiment. The first circular arc, the straight line segment, and the second circular arc together form a smooth, corner-free turning trajectory connecting the end of the first sweep and the start of the next sweep.

The coordinates of waypoints along the turning trajectory may be computed based on a defined (preferably constant) linear velocity of the movement along the trajectory and a sampling frequency (step S1003). Optionally, Gaussian smoothing is applied to the computed turning trajectory by performing a convolution with a Gaussian kernel function (step S1004).

The multiple sweeps which proceed along meridians of the lenticule, connected to each other by the smooth turning trajectories described here, collectively form the scan pattern for performing the lenticular incision. The movable XY-stage 28 and fast-Z scanner 25 are controlled to move the center of the laser scan line according to the scan pattern. During execution of the treatment scan, the laser beam is blanked during the time periods corresponding to the turning trajectories between sweeps (blanking may be accomplished by controlling the laser itself and/or the optical components of the laser delivery system). In other words, the laser cutting stops at end point A, and re-starts at start point E, etc. Accordingly, the start and end point of all sweeps collectively define the outer periphery of the lenticular incision (which may include both an optical zone and a ring shaped transition zone).

To summarize, embodiments of the present invention employ a turning trajectory that includes two circular arcs and a straight line segment between them, each circular arc being tangential to both the corresponding sweep trajectory and the straight line segment, and apply a Gaussian kernel smoothing to the trajectory waypoints, to generate a smooth lenticule cutting trajectory which reduces the acceleration and jerk of the XY actuator.

Figure 11:
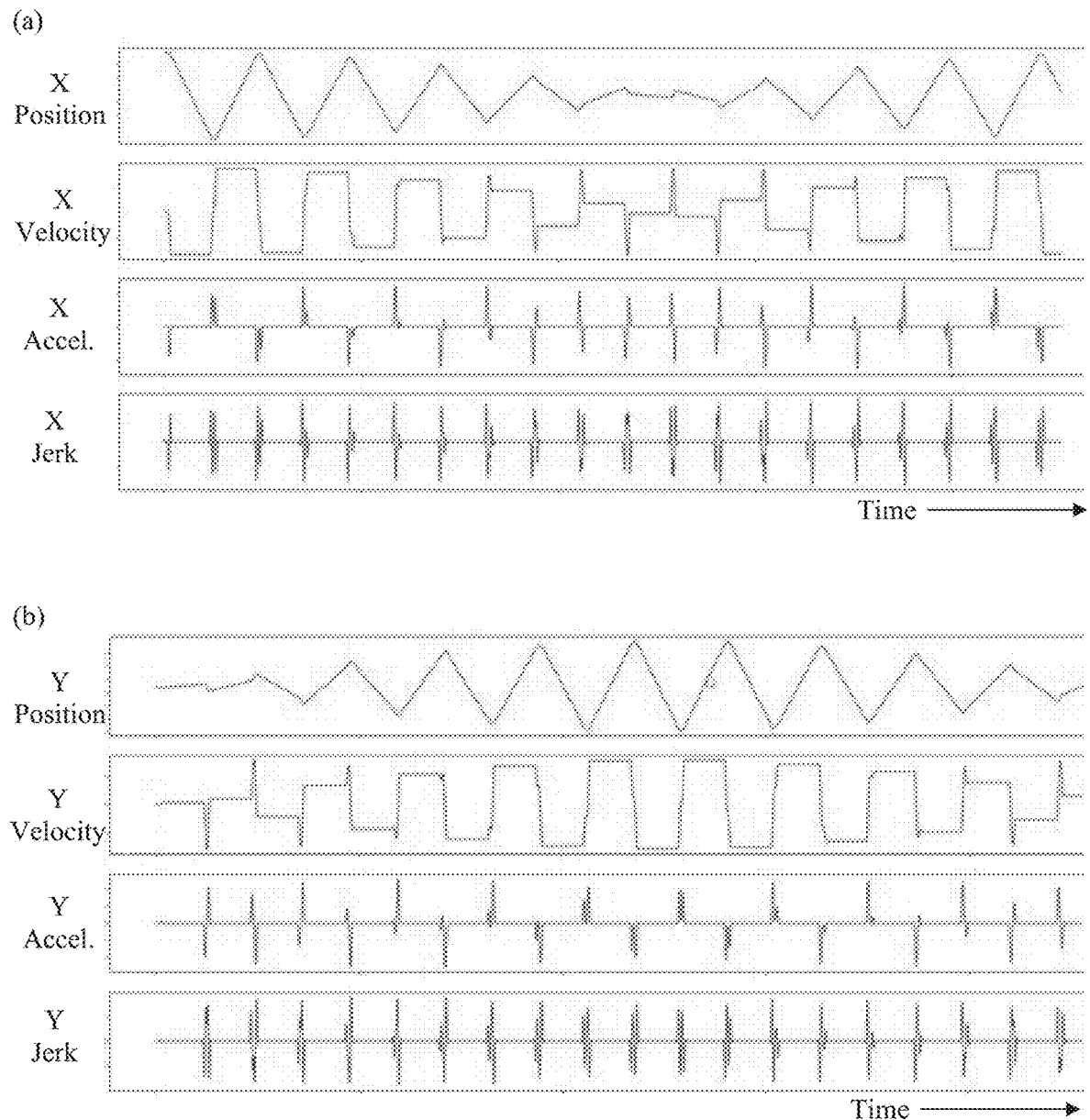
FIGS. 11 and 12 show comparisons of simulated position, velocity, acceleration and jerk in the XY stage during formation of a lenticular incision using straight line turning trajectories according to conventional technology vs. using smooth turning trajectories according to an embodiment of the present invention.
Figure 12:
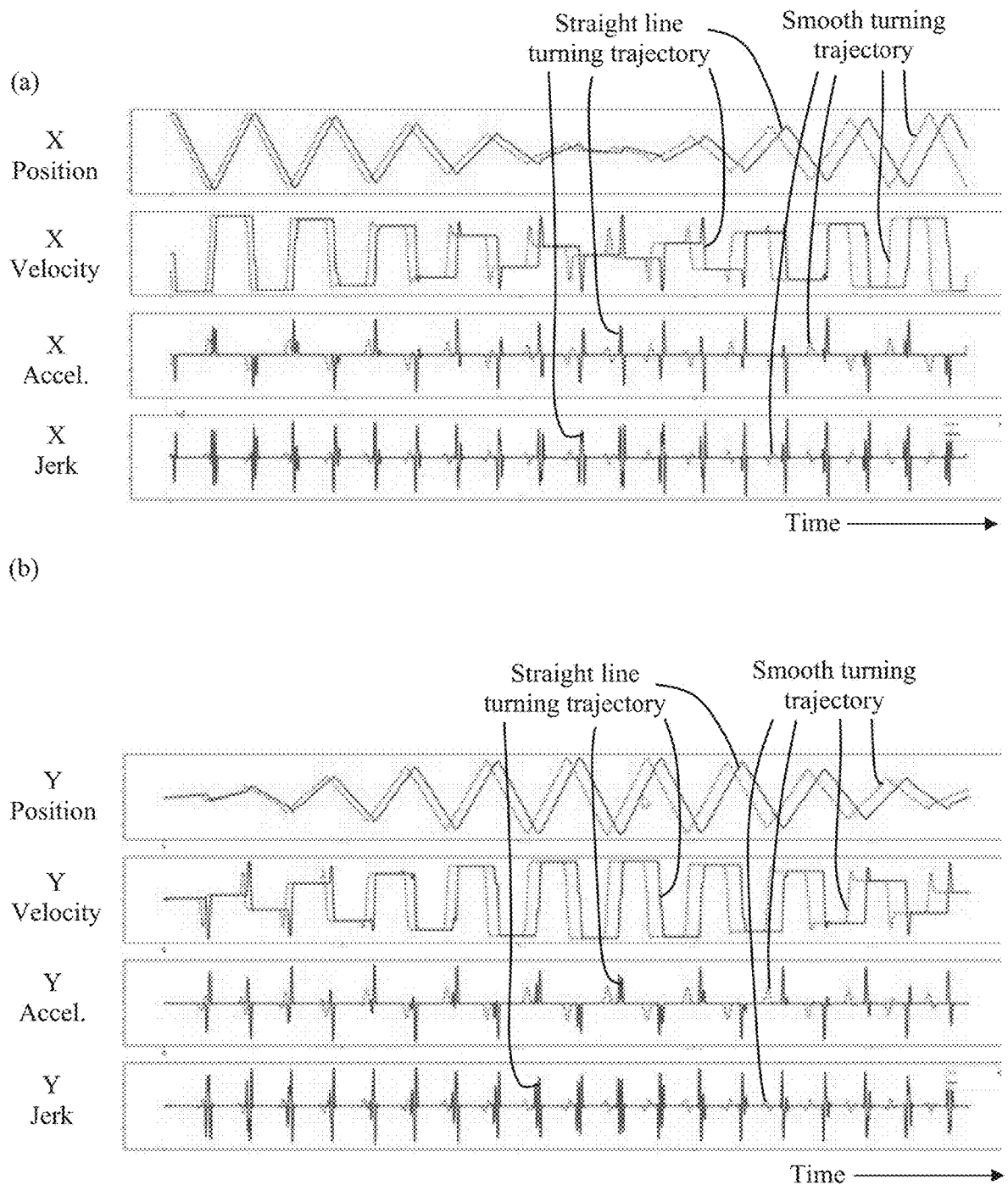

Simulations using actual mechanical parameters for an exemplary XY-stage indicated that as compared to using a straight ling connection, the smooth turning trajectory according to one embodiment of the present invention can reduce the magnitude of acceleration by over one half A comparison of simulated XY stage behavior is shown in FIGS. 11 and 12. FIG. 11 shows simulated position, velocity, acceleration and jerk of the X stage (panel (a)) and Y stage (panel (b)) during formation of a lenticular incision, using straight line turning trajectories according to conventional technology. FIG. 12 shows comparisons of simulated position, velocity, acceleration and jerk of the X stage (panel (a)) and Y stage (panel (b)) during formation of respective lenticular incisions, using straight line turning trajectories (solid lines) vs. smooth turning trajectories according to an embodiment of the present invention (dotted lines).

In some embodiments, the overall lenticular incision procedure is performed in the following steps:
1. Calculate the radius of curvature of the lenticule based on the amount of optical correction, e.g., using Equation (3) for a myopic correction.
2. Select the diameter for the lenticular incision to be extracted.
3. Select laser and optical system parameters, including the laser pulse energy and scan line step parameters described above.
4. Perform bottom surface dissection. In doing so, the fast scan line is preferably kept tangential to the parallels of latitude, and the trajectory of the slow sweep drawn by X, Y, and Z scanning devices moves along the meridians of longitude near south pole in a sequence of 1A to 1B (first sweep of lenticular cut), 2A to 2B (second sweep of lenticular cut), 3A to 3B (third sweep of lenticular cut), and so on, connected by smooth turning trajectories as described above, until the full bottom dissection surface is generated.
5. Perform the lenticule side (edge) incision.
6. Perform the top surface dissection in a similar manner as the bottom dissection is done.
7. Perform the entry incision.

While the method of generating smooth turning trajectories is described above in the context of forming a lenticular incision for a corneal lenticule extraction procedure, the method may also be used other laser assisted ophthalmic procedures where the laser scanning pattern involves trajectory with sharp turning-points. For example, a LASIK procedure involves forming a corneal flap by making, among others, a flat bed cut in the cornea. The bed cut may include multiple sweeps which may be connected to each other using smooth turning trajectories similar to those described above.

All patents and patent applications cited herein are hereby incorporated by reference in their entirety.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. An ophthalmic surgical laser system comprising:
   a laser source configured to generate a pulsed laser beam comprising a plurality of laser pulses;
   a laser delivery system configured to deliver the pulsed laser beam to a target tissue in a subject's eye;
   a high frequency scanner configured to scan the pulsed laser beam back and forth at a predefined frequency;
   an XY-scanner configured to deflect the pulsed laser beam, the XY-scanner being separate from the high frequency scanner;
   a Z-scanner configured to modify a depth of a focus of the pulsed laser beam; and
   a controller configured to control the laser source, the high frequency scanner, the XY-scanner and the Z-scanner to successively form a plurality of sweeps which collectively form at least one lenticular incision of a lens in the subject's eye, the lens having a curved surface that defines an apex and a central axis passing through the apex,
   wherein each sweep is formed by:
      controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the central axis and has a defined distance to the apex, and
      controlling the XY-scanner and the Z-scanner to move a center of the scan line along a meridian of longitude of the lens, the meridian of longitude being a curve that passes through the apex and has a defined angular position around the central axis; and
   wherein the plurality of sweeps are successively formed one after another along the respective meridians of longitude which are different from one another; and
   wherein the controller is further configured to control the XY-scanner to move the center of the scan line along a smooth turning trajectory that connects an end point of a first one of the plurality of sweeps to a start point of a second one of the plurality of sweeps, the turning trajectory including a first circular arc, a straight line segment, and a second circular arc, wherein the first circular arc is tangentially connected to the first sweep at the end point of the first sweep, the second circular arc is tangentially connected to the second sweep at the start point of the second sweep, and the straight line segment is tangentially connected to both the first and second circular arcs.

2. The ophthalmic surgical laser system of claim 1, wherein the controller is further configured to control the laser source and/or the laser delivery system to blank the pulsed laser beam when the center of the scan line is moved along the turning trajectory from the end point of the first sweep to the start point of the second sweep.

3. The ophthalmic surgical laser system of claim 1, wherein the controller is further configured to compute the turning trajectory, including:
   receiving coordinates of a first reference point, a second reference point and the apex as input, the first reference point being located along a direction of the first sweep at a distance from the apex, and a second reference point located along a direction of the second sweep at another distance from the apex; and
   based on the coordinates of the first and second reference points and the apex, and based on at least one predefined geometric parameter, compute the first and second circular arcs and the straight line segment.

4. The ophthalmic surgical laser system of claim 3, wherein the controller is further configured to compute a plurality of waypoints located along the turning trajectory between the end point of the first sweep and the start point of the second sweep based on a linear speed of movement and a sampling frequency.

5. The ophthalmic surgical laser system of claim 3, wherein the controller is further configured to apply Gaussian smoothing to the turning trajectory.

6. The ophthalmic surgical laser system of claim 3, wherein the straight line segment lies on a straight line between the first and second reference points, and the at least one geometric parameter is a distance from the first reference point to a chord of the first circular arc.

7. The ophthalmic surgical laser system of claim 3, wherein the first reference point is the end point of the first sweep and the second reference point is the start point of the second sweep, and the at least one geometric parameter is a radius of a circle of the first circular arc.

8. A method for creating a lenticular incision using an ophthalmic surgical laser system, the method comprising the steps of:
   generating, by a laser source, a pulsed laser beam comprising a plurality of laser pulses;
   delivering the pulsed laser beam to a target tissue in a subject's eye;
   scanning, by a high frequency scanner, the pulsed laser beam back and forth at a predefined frequency;
   deflecting, by an XY-scanner, the pulsed laser beam, the XY-scanner being separate from the high frequency scanner;
   modifying, by a Z-scanner, a depth of a focus of the pulsed laser beam; and
   controlling, by a controller, the laser source, the high frequency scanner, the XY-scanner and the Z-scanner to successively form a plurality of sweeps which collectively form at least one lenticular incision of a lens in the subject's eye, the lens having a curved surface that defines an apex and a central axis passing through the apex, including forming each sweep by:
      controlling the high frequency scanner to deflect the pulsed laser beam to form a scan line, the scan line being a straight line having a predefined length and being tangential to a parallel of latitude of the lens, the parallel of latitude being a circle on the surface of the lens that is perpendicular to the central axis and has a defined distance to the apex, and
      controlling the XY-scanner and the Z-scanner to move a center of the scan line along a meridian of longitude of the lens, the meridian of longitude being a curve that passes through the apex and has a defined angular position around the central axis, and controlling the laser source to periodically blank the pulsed laser beam when the scan line is located within a central area of the lens, wherein the plurality of sweeps are successively formed one after another along the respective meridians of longitude which are different from one another; and controlling, by the controller, the XY-scanner to move the center of the scan line along a smooth turning trajectory that connects an end point of a first one of the plurality of sweeps to a start point of a second one of the plurality of sweeps, the turning trajectory including a first circular arc, a straight line segment, and a second circular arc, wherein the first circular arc is tangentially connected to the first sweep at the end point of the first sweep, the second circular arc is tangentially connected to the second sweep at the start point of the second sweep, and the straight line segment is tangentially connected to both the first and second circular arcs.

9. The method of claim 8, further comprising:

controlling, by the controller, the laser source and/or the laser delivery system to blank the pulsed laser beam when the center of the scan line is moved along the turning trajectory from the end point of the first sweep to the start point of the second sweep.

10. The method of claim 8, further comprising, by the controller, computing the turning trajectory, including:

receiving coordinates of a first reference point, a second reference point and the apex as input, the first reference point being located along a direction of the first sweep at a distance from the apex, and a second reference point located along a direction of the second sweep at another distance from the apex; and based on the coordinates of the first and second reference points and the apex, and based on at least one predefined geometric parameter, compute the first and second circular arcs and the straight line segment.

11. The method of claim 10, further comprising, by the controller, computing a plurality of waypoints located along the turning trajectory between the end point of the first sweep and the start point of the second sweep based on a linear speed of movement and a sampling frequency.

12. The method of claim 10, further comprising, by the controller, applying Gaussian smoothing to the turning trajectory.

13. The method of claim 10, wherein the straight line segment lies on a straight line between the first and second reference points, and the at least one geometric parameter is a distance from the first reference point to a chord of the first circular arc.

14. The method of claim 10, wherein the first reference point is the end point of the first sweep and the second reference point is the start point of the second sweep, and the at least one geometric parameter is a radius of a circle of the first circular arc.

* * * * *